US00PP13608P2

(12) United States Plant Patent
Osiecki

(10) Patent No.: US PP13,608 P2
(45) Date of Patent: Feb. 25, 2003

(54) ANTHURIUM PLANT NAMED 'ATWENTYSIX'

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 09/960,456

(22) Filed: Sep. 24, 2001

(51) Int. Cl.[7] ..... A01H 5/00

(52) U.S. Cl. ..... Plt./365

(58) Field of Search ..... Plt./365, 369

(56) References Cited

PUBLICATIONS

UPOV–ROM GTITM Computer Database 2001/01, GTI JOUVE Retrieval Software, citation(s) for 'Salsa' Feb. 6, 2001.*

* cited by examiner

*Primary Examiner*—Bruce R. Campell
*Assistant Examiner*—A Para

(57) ABSTRACT

A new and distinct cultivar of Anthurium is provided. It is a medium size plant, suitable for production in 15-cm to 20-cm containers, with vigorous growth; full and symmetrical growth habit; relatively early and abundant branching; very early, abundant and year-round flowering; good inflorescence longevity on the plant; and resistance to *Xanthomonas campestris* pv. *dieffenbachiae.* Relatively large, dark pink-red, glossy spathes with cream-colored spadices are held high above foliage on strong, relatively thick peduncles.

3 Drawing Sheets

BOTANICAL CLASSIFICATION/CULTIVAR DESIGNATION

Anthurium hybrid cultivar Atwentysix.

BACKGROUND OF THE INVENTION

This invention relates to a new and distinct cultivar of anthurium plant, botanically known as Anthurium hybrid, and hereinafter referred to by the cultivar name 'Atwentysix'.

The new cultivar is a product of a planned breeding program conducted by the Inventor in Altha, Fla. The objective of the program was to develop a vigorous pot Anthurium cultivar, resistant to *Xanthomonas campestris* pv. *dieffenbachiae,* with attractive foliage and attractive spathes well visible above foliage.

The new Anthurium was discovered and selected by the Inventor in 1998 as a seedling within the progeny of a cross made in 1995 in a controlled environment in Altha, Fla. The female parent was a proprietary Anthurium seedling selection identified by the code number 91-11-48, obtained by the Inventor in the same breeding program, not patented. The male parent was a selected clone of Anthurium hybrid cultivar Lady Jane identified by the code number 941, not patented.

Asexual propagation of 'Atwentysix', since 1998, by means of tissue culture in Altha, Fla. has established that the unique characteristics of this new cultivar are in fact stable and reproduced true to type in successive generations.

SUMMARY OF THE INVENTION

The new Anthurium cultivar has not been observed under all possible environmental conditions. The phenotype may vary somewhat with variations in environment and/or horticultural practices such as temperature, light intensity, day length, fertilization, irrigation, propagation procedures etc., without any variance in genotype.

The following traits have been repeatedly observed and in combination distinguish 'Atwentysix' as a new and distinct cultivar of pot Anthurium:

1. Medium size plant, appropriate for 15-cm to 20-cm containers;
2. Vigorous growth;
3. Abundant branching;
4. Very early, abundant and year-round flowering;
5. Relatively large, dark pink-red, glossy spathes with good longevity on the plant;
6. Spathes held high above foliage on strong, relatively thick peduncles;
7. Cream-colored spadices;
8. Resistance to *Xanthomonas campestris* pv. *dieffenbachiae.*

Plants of 'Atwentysix' are distinguished from plants of the female parent, a proprietary Anthurium seedling selection identified by the code number 91-11-48, by its smaller size; earlier and more abundant branching; earlier flowering; smaller leaf blades; glossier, more pinkish spathes; and cream-colored spadices as opposed to dark purple spadices of 91-11-48.

Plants of 'Atwentysix' are distinguished from plants of the male parent, a selected clone of Anthurium hybrid cultivar Lady Jane identified by the code number 941, by its more vigorous growth; earlier and more abundant branching; earlier and more abundant flowering; larger, more deltoid spathes, with lower length:width ratio, darker pink-red, held higher above foliage; and cream-colored spadices as opposed to pinkish-cream spadices of 'Lady Jane' # 941.

The new cultivar can be compared to its siblings disclosed in the concurrent U.S. Plant Patent applications as the cultivars 'Favorita' (Ser. No. 09/961,829) and 'Valentine' (Ser. No. 09/960,455). The comparisons were made on plants of the same age, grown side-by-side under the same greenhouse conditions in Altha, Fla.

Plants of the new Anthurium cultivar differ from plants of the cultivar Favorita in the following characteristics:

1. Plants of 'Atwentysix' start branching later than plants of 'Favorita'.

2. Plants of 'Atwentysix' flower less abundantly than plants of 'Favorita'.

3. Foliage of 'Atwentysix' is shorter than foliage of 'Favorita' due to shorter petioles.

4. Leaf blades of 'Atwentysix' are lighter green and less glossy than leaf blades of 'Favorita'.

5. Spathes of 'Atwentysix' are larger and held higher above foliage than spathes of 'Favorita'.

6. Spathes of 'Atwentysix' are dark pink-red, whereas spathes of 'Favorita' are orange-red.

7. Spadices of 'Atwentysix' are cream-colored, whereas spadices of 'Favorita' are pink-purple.

Plants of the new Anthurium cultivar differ from plants of the cultivar Valentine in the following characteristics:

1. Plants of 'Atwentysix' are larger, branch later and less abundantly and have more open growth habit than plants of 'Valentine'.

2. Plants of 'Atwentysix' flower earlier, but less abundantly than plants of 'Valentine'.

3. Leaf blades of 'Atwentysix' are larger than leaf blades of 'Valentine' and have greater length:width ratio.

4. Peduncles of 'Atwentysix' are thicker, stronger and longer than peduncles of 'Valentine'.

5. Spathes of 'Atwentysix' are held higher above foliage, are larger and have shorter longevity on the plant than spathes of 'Valentine'.

6. Spathes of 'Atwentysix' are dark pink-red, whereas spathes of 'Valentine' are deep red.

The new cultivar can be compared to the known Anthurium cultivar '75-10', disclosed in U.S. Plant Pat. No. 9,355, a/k/a Red Hot™. The comparisons were made on plants of the same age, grown side-by-side under the same greenhouse conditions in Altha, Fla.

Plants of the new Anthurium cultivar differ from plants of the cultivar 75-10 in the following characteristics:

1. Foliage of 'Atwentysix' is shorter than foliage of '75-10' due to shorter petioles.

2. Inflorescences of 'Atwentysix' are of a good quality from the onset of flowering, whereas several first spathes produced by plants of '75-10' are very small and deformed.

3. Spathes of 'Atwentysix' are held higher above foliage than spathes of '75-10'.

4. Peduncles of 'Atwentysix' are green with varying amounts of purplish and brownish coloration, whereas peduncles of '75-10' are dark purple.

5. Spathes of 'Atwentysix' are more deltoid, with lower length:width ratio, glossier and are dark pink-red, whereas spathes of '75-10' are dull red.

6. Spathes of 'Atwentysix' maintain color and gloss longer than spathes of '75-10'.

7. Spadices of 'Atwentysix' are cream-colored, whereas spadices of '75-10' are dark purple.

BRIEF DESCRIPTION OF THE PHOTOGRAPHS

The accompanying photographs illustrate the appearance of the new Anthurium cultivar, showing the colors as true as it is reasonably possible in color reproductions of this type. Colors in the photographs may appear slightly different from the color values cited in the botanical description, which accurately describe the actual colors of the plants of the new cultivar. The plant of 'Atwentysix' depicted in the photographs was approximately 15 months from planting a single tissue culture-produced microcutting, and was grown in a 15-cm container.

In the photographs:

BOTANICAL DESCRIPTION OF THE NEW CULTIVAR

Figure 1:
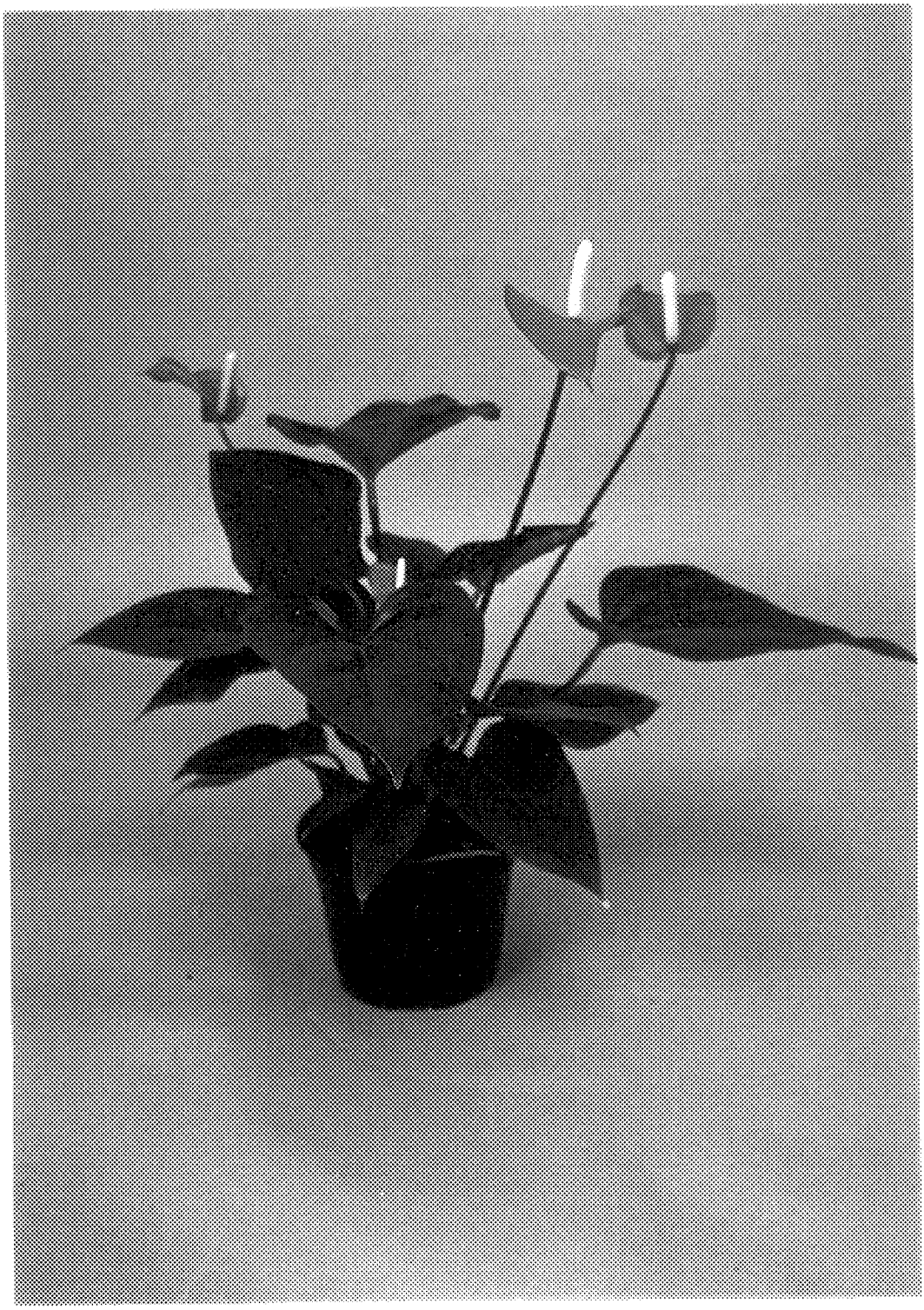
FIG. 1 depicts the whole plant.
Figure 2:
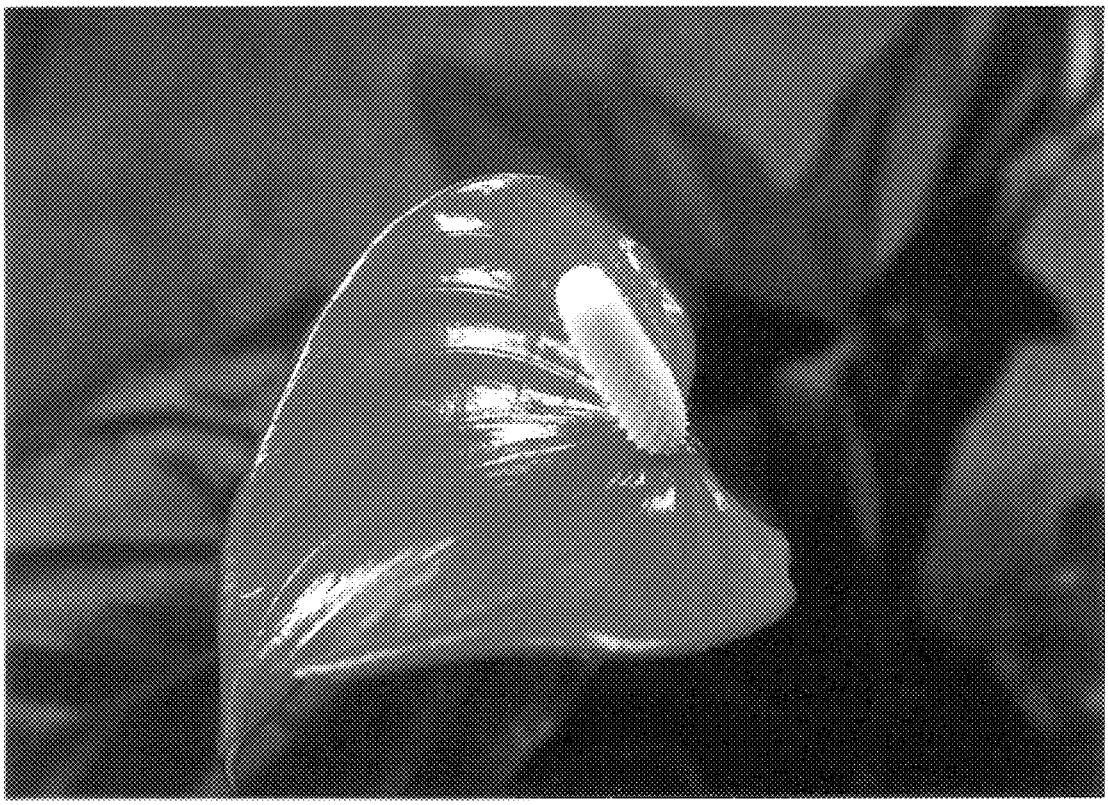
FIG. 2 illustrates the mature inflorescence.
Figure 3:
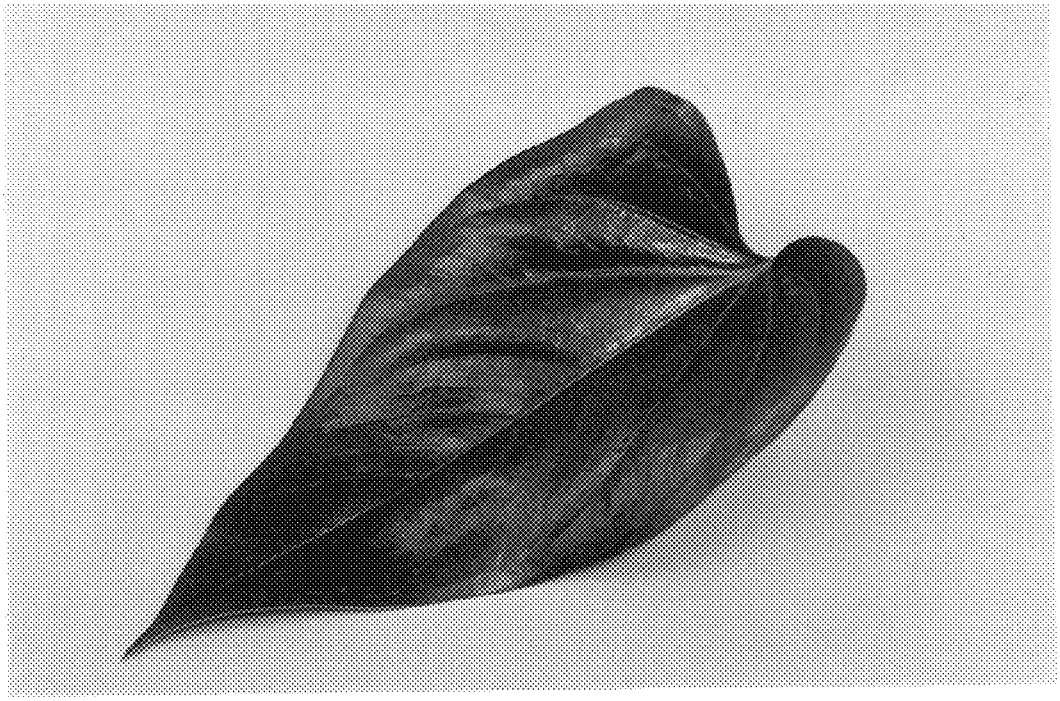
FIG. 3 illustrates the adaxial side of a mature leaf.
Figure 4:
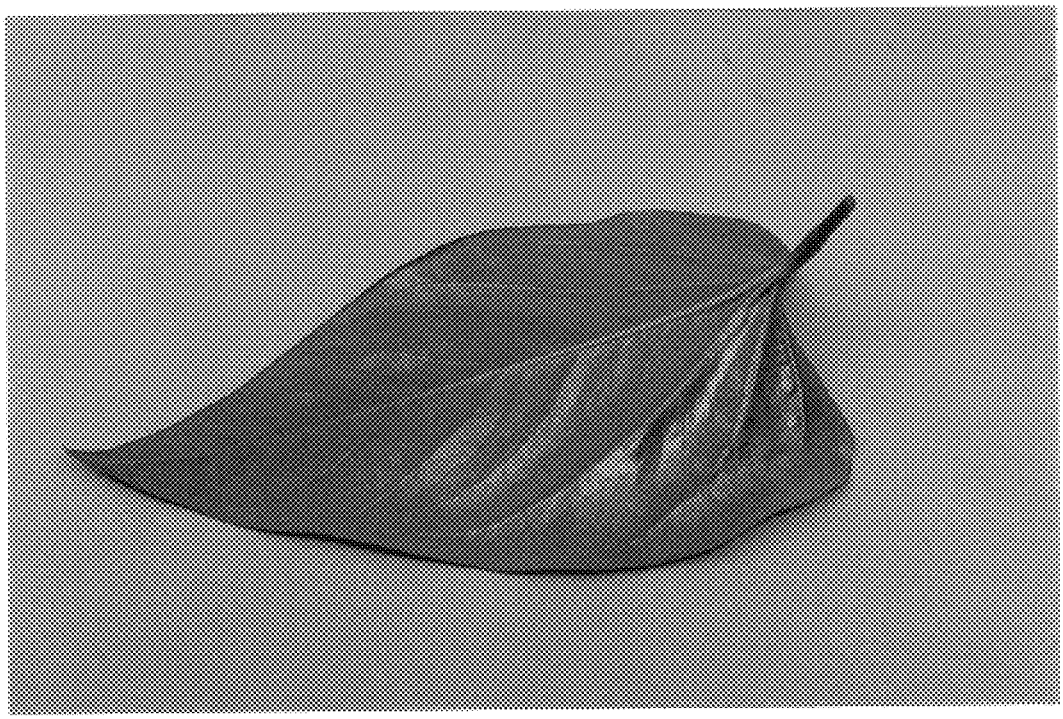
FIG. 4 illustrates the abaxial side of a mature leaf.

The following observations and measurements were recorded in February and March 2001, on plants grown in a polycarbonate-covered greenhouse in Altha, Fla. under conditions which closely approximate those used in commercial horticultural practice. During growth of these plants day temperature in the greenhouse ranged between 23 and 28° C., night temperature ranged between 20 and 23° C., and light level ranged between 800 and 1500 foot-candles. Plants used for these observations were grown as single plants in 15-cm containers and were about 15 months from planting tissue culture-produced microcuttings.

Mature, fully developed plant organs were used for the following observations and measurements unless otherwise indicated. Numerical measurements represent means from typical plants of 'Atwentysix'. Color references are made to The R.H.S. Colour Chart, except where general color terms of ordinary significance are used. Color values were determined under natural light of approximately 860 to 2000 foot-candles.

Parentage:

*Female parent.*—Proprietary Anthurium seedling selection identified by the code number 91-11-48 (not patented).

*Male parent.*—Selected clone of Anthurium hybrid cultivar Lady Jane, identified by the code number 941 (not patented).

Propagation:

*Type.*—Plant tissue culture.

*Time to produce a rooted liner.*—Summer: About 13 to 14 weeks at about 25 to 30° C. soil temperature. Winter: About 15 to 16 weeks at about 22 to 27° C. soil temperature.

Plant description:

*Growth habit.*—Medium size plant, relatively open when young, well branched and full later. Appropriate for 15-cm to 20-cm containers.

*Plant size.*—Height, soil level to top of inflorescences: About 40.3 cm. Height, soil level to top of leaf canopy: About 26.4 cm. Diameter (area of spread): About 57.8 cm.

*Plant vigor.*—Vigorous

*Crop time.*—About thirteen months are needed to produce a finished plant in a 15-cm container from a single tissue culture-produced microcutting.

Foliage description:

*Petiole.*—Size: About 17.9 cm long, about 4.4 mm in diameter immediately below geniculum. Geniculum: About 2.2 cm long, about 5.5 mm in diameter at the base. Not very prominent. Color: Newly unrolled leaf, adaxial: Similar to or slightly more brown than 146A. Geniculum approximately 146A. Newly unrolled leaf, abaxial: Between 146A and 144A near base; distally lighter (approximately 144A). Geniculum approximately 144A. Mature leaf, adaxial: Approximately 146A near base with the amount of purplish anthocyanin coloration increasing distally. Geniculum approximately 146A. Petiole wings between 146A and 146B. Mature leaf, abaxial: Between 147A and 146A near base. Distally lighter and more yellow (between 144A and 146B below geniculum). Geniculum approximately 144A.

*Leaf blade.*—Shape: Ovate; apex acuminate; base cordate with truncate tendencies; margin entire. Size: About 25.4 cm long, about 14.2 cm wide; length-:width ratio about 1.8:1. Aspect: Most leaves approximately horizontal; some slightly oblique with apices pointing down; lobes curving upwards. Texture/surface: Thick, leathery, glabrous. Venation: Pinnipalmate; prominent primary veins. Color: Newly unrolled leaf, adaxial: Lighter and more yellow than 147A but darker and greener than 146A. Newly unrolled leaf, abaxial: Most similar to, but usually greener and sometimes lighter than 146B. Mature leaf, adaxial: Much darker than 147A with contrasting veins in proximal zone (between 144A and 146B). Various amounts of purplish anthocyanin coloration near petiole juncture. Mature leaf, abaxial: Between 144A, 146A and 146B. Most midrib and proximal portions of primary veins between 146C, 146D and 144B.

Inflorescence description:

*Inflorescence arrangement.*—Spathes with spadices held high above foliage on strong, relatively thick peduncles.

*Flowering.*—Exceptionally early, abundant and year-round. Flowers naturally in 10-cm containers about 8 months after planting tissue culture-produced microcuttings. At 15 months about 3.8 inflorescences per plant, including buds.

*Spathe longevity.*—In spring spathe maintains color and gloss for approximately 2.5 months following bud appearance.

*Peduncle.*—Size: About 35.0 cm long, about 3.9 mm in diameter immediately below spathe. About 4.5 mm of peduncle between spathe and spadix base in front. Color: Just before spathe unrolling, front: Between 144A and 146A near base. Distally darker, often with slight brownish anthocyanin coloration. 144B immediately below spathe. Just before spathe unrolling, back: Approximately 146A near base. Between 146B and 144A in distal half. Approximately 144B immediately below spathe. Mature inflorescence, front: Darker than 146A near base, distally with variable amount of brownish and/or purplish anthocyanin coloration. Most distal zone is usually between 152C and 152D, often flushed with some orange-red coloration. Approximately 47A between spathe base and spadix base. Mature inflorescence, back: Similar to 146A near base, distally with variable amounts of brownish and/or purplish anthocyanin coloration. Most distal zone varies between 144A and 144B and is flushed with variable amount of red (approximately 43B). Often predominantly red (approximately 43B) at juncture with spathe.

*Spathe.—Shape: Between ovate and deltoid, asymmetric, often twisted; apex between acuminate and aristate; base cordate; margin entire. Size: About* 9.1 cm long, about 7.7 cm wide; ratio length-:width about 1.2:1. Texture/Surface: Glabrous; very glossy; usually wavy and very slightly puckered. Color: Closed bud (before unrolling): Uneven color gradually merging from the darkest (51A or darker) near apex to lightest (51D or lighter) near base. Veins green (approximately 144A) near base. Newly unrolled spathe, front surface: Varies between 47A and 47B with approximately 1 mm-wide darker line (46A) along the margin. Newly unrolled spathe, back surface: Uneven color varying between 51B, 51C and 51D. Most veins much darker (approximately 47A). Area around peduncle juncture between 47A and 47B. Less than 1 mm-wide line along margin approximately 46A. Mature spathe, front surface: Approximately 47A with 1 mm-wide darker (approximately 46A) line along margin. Mature spathe, back surface: Uneven color varying between 51B, 51C and 51D. Most veins much darker (approximately 47A). Area around peduncle juncture approximately 47A. Less than 1 mm-wide line along margin approximately 46A.

*Spadix.*—Shape: Cylindrical, usually straight, very slightly tapering at apex; cross section rounded. Size: About 4.7 cm long, about 10.3 mm in diameter. Flower density: About 16 to 18 flowers per linear 2 cm of spadix (mid-section). Color: Young, immediately after spathe unrolling: Approximately 21D. Mature inflorescence: Proximal zone, with pistils, between 158B and 158C. Distal zone without pistils approximately 18A.

*Botanical flower.*—Perianth: Perianth of an individual flower appears on the spadix surface as almost a diamond shape, about 2.5 mm long and 2 mm wide. Pistil: About 2.1 mm long and about 1.1 mm in diameter; protrudes fraction of a millimeter beyond perianth; cream-colored, translucent. Stigma small. Stamens: About 1.2 mm long and 0.7 mm wide; cream-colored, translucent; flat; firmly pressed against pistil. Do not protrude beyond perianth until pollen dehiscence. Pollen: Aging inflorescences occasionally produce small amounts of whitish pollen. Fragrance: Moderate to strong, pleasant.

*Seed.*—Spontaneous seed development not observed.

Roots description: Thick, fleshy main roots, pinkish-cream with yellow root caps. Abundant, relatively thick, cream-colored lateral roots.

Disease and insect resistance: Plants of 'Atwentysix', which are grown in commercial greenhouses, have not shown any unusual susceptibility to pathogens or insects common to Anthurium. In the greenhouse tests plants of 'Atwentysix' have demonstrated high degree of resistance to *Xanthomonas campestris* pv. *dieffenbachiae*.

I claim:

1. A new and distinct cultivar of Anthurium plant named 'Atwentysix' as described and illustrated herein.

* * * * *